United States Patent [19]
Oh et al.

[11] Patent Number: 6,018,038
[45] Date of Patent: Jan. 25, 2000

[54] INCOMPATIBLE PLANT AND PATHOGEN INTERACTION RELATED GENE

[75] Inventors: Boung-Jun Oh; Moon Kyung Ko; Igor Kostenyuk, all of Kwangju, Rep. of Korea

[73] Assignee: Korea Kumho Petrochemical Co., Ltd., Seoul, Rep. of Korea

[21] Appl. No.: 09/225,244

[22] Filed: Jan. 4, 1999

[51] Int. Cl.[7] .......................... C07H 21/04; C07K 14/00; C12P 21/06; C12N 1/20; C12N 15/00
[52] U.S. Cl. .................. 536/23.6; 536/23.2; 530/350; 435/69.1; 435/252.3; 435/320.1
[58] Field of Search ................... 536/23.6, 23.2; 530/350; 435/69.1, 252.3, 320.1

[56] References Cited

PUBLICATIONS

Salzman, et al., *Plant Physiol.*, 117: 465–472 (1998).
Meyer, et al., *Plant Physiol.*, 112: 616–622 (1996).
Oh, et al., *J. Phytopathology*, 146: 301–303 (1998).
Baudouini, et al., *Eur. J. Biochem.*, 248: 700–706 (1997).
Pontler, et al., *The Plant Journal*, 5(4): 507–521 (1994).
Manandhar, et al., *Plant Disease*, 79: 380–383 (1995).
Brick, et al., *FEBS Letters*, 377 : 475–480 (1995).

*Primary Examiner*—Ponnathapu Achutamurthy
*Assistant Examiner*—Tekchand Saidha
*Attorney, Agent, or Firm*—Kenyon & Kenyon

[57] ABSTRACT

The present invention relates to a cDNA clone, designated to icc13 (incompatible Capsicum annuum-Colletotrichum gloeosporioides interactions) gene and individual component; thereof including its coding region and its gene product; modification thereto; application of said gene, coding region and modifications thereto; DNA construct, vectors and transformed plants each comprising the gene or part thereof.

1 Claim, 6 Drawing Sheets

```
  1  TTATCTGTGTGATCAATTATTATGGCTAGCCAAAGTTTTGTTCCTCCAATTTTTGAAAAT    60
  1                             M  A  S  Q  S  F  V  P  P  I  F  E  N    13
 61  CCCTTTCTTAACATTGAAGAATTAGCAGGTGACACAATTGTACGTAAACCTGAACCCCTC   120
 14   P  F  L  N  I  E  E  L  A  G  D  T  I  V  R  K  P  E  P  L    33
121  ACACAAGCCAATTCTGATCCCAATGGCACGTCCTTAGTTGTATCTAAAGACGTAGACCTT   180
 34   T  Q  A  N  S  D  P  N  G  T  S  L  V  V  S  K  D  V  D  L    53
181  GACATCAACAAAAAGACATGGCTGCGAATATACGTCCCACAACGAATAATCACAAATCAT   240
 54   D  I  N  K  K  T  W  L  R  I  Y  V  P  Q  R  I  I  T  N  H    73
241  AATGATGATGAAAAATTGCCTGTCATTTTCTACTACCATGGTGGAGGCTTTGTTTTCTTC   300
 74   N  D  D  E  K  L  P  V  I  F  Y  Y  H  G  G  G  F  V  F  F    93
301  CATGCCAATAGTTTTGCCTGGGATTTGTTTTGTCAAGGACTTGCTGGAAACCTTGGGGCA   360
 94   H  A  N  S  F  A  W  D  L  F  C  Q  G  L  A  G  N  L  G  A   113
361  ATGGTTATCTCCCTTGAATTTCGTCTGGCCCCTGAAAATCGCCTTCCTGCAGCTTACGAC   420
114   M  V  I  S  L  E  F  R  L  A  P  E  N  R  L  P  A  A  Y  D   133
421  GATGCCATGGATGGGTTATATTGGATTAAATCAACTCAAGATGAATGGGTCCGAAAATAT   480
134   D  A  M  D  G  L  Y  W  I  K  S  T  Q  D  E  W  V  R  K  Y   153
481  TCAGATTTGAGTAACGTTTATCTTTTTGGATCTAGTTGCGGTGGAAACATAGCTTACCAT   540
154   S  D  L  S  N  V  Y  L  F  G  S  S  C  G  G  N  I  A  Y  H   173
541  GCAGGGTTACGGGTAGCAGCTGGGGCATATAAAGAACTAGAGCCAGTGAAGATCAAAGGG   600
174   A  G  L  R  V  A  A  G  A  Y  K  E  L  E  P  V  K  I  K  G   193
601  CTAATTTTGCATCAACCATATTTCAGTGGAAAAAACAGGACAGAATCTGAAGAGAAGCTA   660
194   L  I  L  H  Q  P  Y  F  S  G  K  N  R  T  E  S  E  E  K  L   213
661  AAGGATGATCAACTTTTGCCATTACATGCAATTGACAAAATGTTCGACTTGTCCTTGCCA   720
214   K  D  D  Q  L  L  P  L  H  A  I  D  K  M  F  D  L  S  L  P   233
721  AAAGGGACACTTGATCATGATCATGAATATTCCAATCCATTTCTTAATGGAGGGTCCAAG   780
234   K  G  T  L  D  H  D  H  E  Y  S  N  P  F  L  N  G  G  S  K   253
781  CATTTAGATGATGTGATCGCACAAGGCTGGAAGATTCTTGTAACTGGTGTCTCTGGAGAT   840
254   H  L  D  D  V  I  A  Q  G  W  K  I  L  V  T  G  V  S  G  D   273
841  CCTCTGGTTGATAATGCGCGCAACTTTGCAAATTTTATGGAAGAAAAAGGCATAAAAACT   900
274   P  L  V  D  N  A  R  N  F  A  N  F  M  E  E  K  G  I  K  T   293
901  TTCAAGCTCTTTGGAGATGGTTATCATGCAATTGAGGGGTTTGAACCATCAAAGGCAGCA   960
294   F  K  L  F  G  D  G  Y  H  A  I  E  G  F  E  P  S  K  A  A   313
961  GCTTTAATTGGCGCCACCAAAGATTTCATATGTGCTACTACAAATTAAAAATATGTAACG  1020
314   A  L  I  G  A  T  K  D  F  I  C  A  T  T  N                  328
1021 TAGCATCCTGCTAGCGTTGTGTTTGTTTCATTTCCTTCAAATAAATCAAGTGAGCTTCTT  1080
1081 TGTGCAAATAAGAGGGGTTTACACCCTCCTTCCTGTTAGAGATTACTTTAAAATATTATA  1140
1141 TTTCTCTTGAAGATCAAAGTTTTAGAGATGAGTTATTGCTGAAAAAAAAAAAAAAAAAAA  1200
1201 AAAAAAAAAAAAAAAAA                                             1217
```

FIG. 1

```
Pep     1                MASQSF-----------VPPIFE-------------NPFLNIEELAGDTI  26
Ara-1   1                MEAP-----------PPSSDP-------------YKFLNITLNSDGSL    24
Ara-2   1                MSRDS----------PPAFDP-------------YKHLNITINPNGSC    25
Tob     1                MVHEKQV-----------IEEVSG-------------WLRVFEDGSVDRTW 27
Bac     1    MSRCGRRAELLHAAGTGSGSASFPMSAAPSSSPDAPATPGLPSSPLDPQVAALLELIARA    60

Pep     27   VR-----------KPEPLTQANSDPNGTSL-VVSKDVDLDINKK--TWLRIYVPQRIIT    71
Ara-1   25   TRH-----------RDFPKLPPTEQ---------SKDIPLNQTNN--TFIRIFKPRNIPP  62
Ara-2   26   TRH-----------FVWPRVEPDPDPCPGKL-AASKDVTINHETG--VSVRIFRPTNLPS  71
Tob     28   TGP---------PEVKFMAEPVPPHDYF IDGVAVKDVVADEKSG--SRLRIYLPERNDN  75
Bac     61   KRPPIHAMEPEDAKIAYEKSAPILDINPPP-VYMAEDLLAPARDGHAIPLRLYTPREASW 119
Consensus                                         D           R P

•••••
Pep     72   NHNDDEKLPVIFYYHGGGFVFFHANSFAWDLFCQGLAGNLGAMVISLEFRLAPENRLPAA 131
Ara-1   63   E----SKLPILVYFHGGGFILYSAASAPFHESCTKMADRLQTIILSVEYRLAPEHRLPAA 118
Ara-2   72   NDNAVARLPIIIHLHCSGWILYPANSAANDRCCSQMASELTVIVVSVHYRLPPEHRLPAQ 131
Tob     76   S---ASKLPVILHFQGGGFCVSHADWFMYYTVYTRLARAAKAIIVSVFLPLAPEHRLPAA 132
Bac     120  T----EPLPLLVYFHGGGFTVGSVDS--HDPLCRLLCGQADCMVLSVDYRLGPQWRFPTA 173
Consensus         LP       G G                         S      L P RP

•••••
                                                          *
Pep     132  YDDAMDGLYWIKS------TQ---DEWVRKYSDLSNVYLFGSSCGGNIAYHAGLRVAAGA 182
Ara-1   119  YEDAVEAILWLRDQARGPINGGDCDTWLKDGVDFSKCYVMGSSSGGNIVYNVALRVVD-- 176
Ara-2   132  YDDALDALLWVKQQVVDSTNG---EPWLKDYADFSRCYICGSSNGANIAFQLALRSLD-- 186
Tob     133  CDAGFAALLWLRDLSR--QQG--HEPWLNDYADFNRVFLIGDSGGNIVHQVAVKAGE-- 186
Bac     174  ANDAFDVLHWVFA-----EAG-------RLGADPARIAVGGDSAGGTLAAACAVEARN-- 219
Consensus            W                D        G S G Pep     183  YKELEPVKIKGLILHQPYFSGKNRTESEEKLKDDQLLPLHAIDKMFDLSLPKGTLDHDHE 242
Ara-1   177  -TDLSPVKIQGLIMNQAFFGGVEPSDSESRLKDDKICPLPATHLLWSLCLPDG-VDRDHV 234
Ara-2   187  -HDLTPLQIDGCVFYQPLFGGKTRTKSELKNFADPVMPVPAVDAMWELSLPVG-VDRDHR 244
Tob     187  -ENLSPMRLAGAIPIHPGFVRSYRSKSELEQEQTPFLTLDMVDKFLGLALPVG-SNKDHQ 244
Bac     220  -AGLAPVLQ---LLIYPGTCARQDTPSHRALADGYLLTADMIRWFFAQYLDQE-ASRDDW 274
Consensus     L P                    S                        L D

*
Pep     243  YSNPFLNGGSKHLDDVIAQGWKILVTGVSGDPLVDNARNFANFMEEKGIKTFKLFG-DGY 301
Ara-1   235  YSNPIKS-SGPQEKDKMGRFPSTLINGYGGDPLVDRQRHVAEMLKGRGVVHVETRFDKGF 293
Ara-2   245  YCNPLG--YLPQ-KEKVGRLGRCLVIGYGGDTSLDRQQDFVNLLVAAGVRVEARFDDAGF 301
Tob     245  ITCPMG---EAAPAVEELKLPPYLYCVAEKDLIKDTEMEFYEAMKKGEKDVELFINNGVG 301
Bac     275  RFAPLD---GGGAGAEVRGTCPAWIAVAGYDPLHDEGVAYAEKLRAAGVAATLADYPGMI 331
Consensus         P                           D D

*
Pep     302  HAIEGFE--------PSKAAALIGATKDFICATTN           328
Ara-1   294  HACELFD--------GNKAKALYETVEAFMKSCSSTGPSSNSNM  329
Ara-2   302  HSIELVD--------PRRAVALLNMIRDFIS               324
Tob     302  HSFYLNKIAVRMDPVTGSETEKLYEAVAEFINKH            335
Bac     332  HDFFKLG------RFVPAVAQAHAEAVAALRAAFGTPHN       364
Consensus    H
```

FIG.2

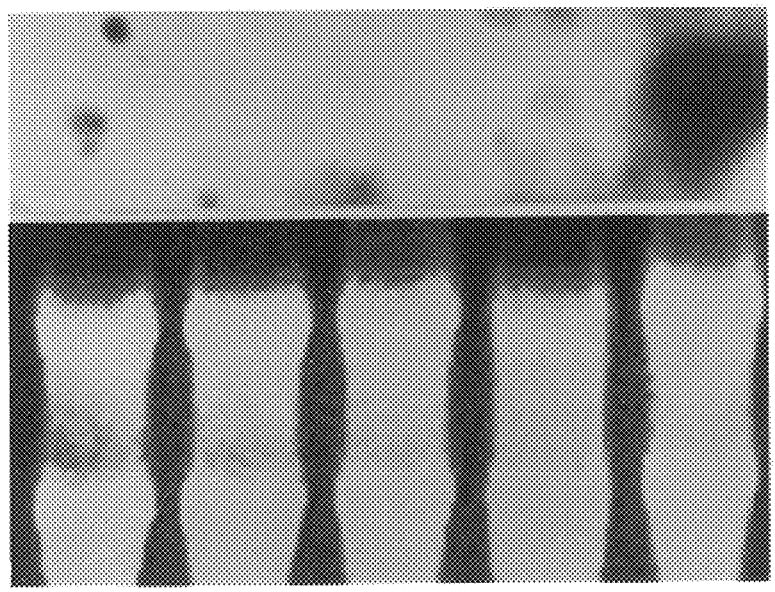
FIG.5

SEQUENCE LISTING

<160> NUMBER OF SEQ ID NOS: 2

<210> SEQ ID NO 1
<211> LENGTH: 1217
<212> TYPE: DNA
<213> ORGANISM: Capsicum annuum

<400> SEQUENCE: 1

```
ttatctgtgt gatcaattat tatggctagc caaagttttg ttcctccaat ttttgaaaat      60
ccctttctta acattgaaga attagcaggt gacacaattg tacgtaaacc tgaacccctc     120
acacaagcca attctgatcc caatggcacg tccttagttg tatctaaaga cgtagacctt     180
gacatcaaca aaaagacatg gctgcgaata tacgtcccac aacgaataat cacaaatcat     240
aatgatgatg aaaaattgcc tgtcattttc tactaccatg gtggaggctt tgttttcttc     300
catgccaata gttttgcctg ggatttgttt tgtcaaggac ttgctggaaa ccttgggca     360 atggttatct cccttgaatt tcgtctggcc cctgaaaatc gccttcctgc agcttacgac     420
gatgccatgg atgggttata ttggattaaa tcaactcaag atgaatgggt ccgaaaatat     480
tcagatttga gtaacgttta tcttttgga tctagttgcg gtggaaacat agcttaccat     540
gcagggttac gggtagcagc tggggcatat aaagaactag agccagtgaa gatcaaaggg     600 ctaatttgc atcaaccata tttcagtgga aaaaacagga cagaatctga agagaagcta     660
aaggatgatc aacttttgcc attacatgca attgacaaaa tgttcgactt gtccttgcca     720
aaagggacac ttgatcatga tcatgaatat tccaatccat ttcttaatgg agggtccaag     780
catttagatg atgtgatcgc acaaggctgg aagattcttg taactggtgt ctctggagat     840
cctctggttg ataatgcgcg caactttgca aattttatgg aagaaaaagg cataaaaact     900
ttcaagctct ttggagatgg ttatcatgca attgaggggt ttgaaccatc aaaggcagca     960
```

-continued

```
gctttaattg gcgccaccaa agatttcata tgtgctacta caaattaaaa atatgtaacg    1020
tagcatcctg ctagcgttgt gtttgtttca tttccttcaa ataaatcaag tgagcttctt    1080
tgtgcaaata agagggtttt acaccctcct tcctgttaga gattacttta aatattata     1140 tttctcttga agatcaaagt tttagagatg agttattgct gaaaaaaaaa aaaaaaaaa     1200 aaaaaaaaaa aaaaaa                                                    1217
```

<210> SEQ ID NO 2
<211> LENGTH: 328
<212> TYPE: PRT
<213> ORGANISM: Capsicum annuum

<400> SEQUENCE: 2

```
Met Ala Ser Gln Ser Phe Val Pro Pro Ile Phe Glu Asn Pro Phe Leu
  1               5                  10                  15

Asn Ile Glu Glu Leu Ala Gly Asp Thr Ile Val Arg Lys Pro Glu Pro
             20                  25                  30

Leu Thr Gln Ala Asn Ser Asp Pro Asn Gly Thr Ser Leu Val Val Ser
         35                  40                  45

Lys Asp Val Asp Leu Asp Ile Asn Lys Lys Thr Trp Leu Arg Ile Tyr
     50                  55                  60

Val Pro Gln Arg Ile Ile Thr Asn His Asn Asp Asp Glu Lys Leu Pro
 65                  70                  75                  80

Val Ile Phe Tyr Tyr His Gly Gly Phe Val Phe His Ala Asn
                 85                  90                  95

Ser Phe Ala Trp Asp Leu Phe Cys Gln Gly Leu Ala Gly Asn Leu Gly
                100                 105                 110

Ala Met Val Ile Ser Leu Glu Phe Arg Leu Ala Pro Glu Asn Arg Leu
            115                 120                 125

Pro Ala Ala Tyr Asp Ala Met Asp Asp Gly Leu Tyr Trp Ile Lys Ser
        130                 135                 140

Thr Gln Asp Glu Trp Val Arg Lys Tyr Ser Asp Leu Ser Asn Val Tyr
145                 150                 155                 160

Leu Phe Gly Ser Ser Cys Gly Gly Asn Ile Ala Tyr His Ala Gly Leu
                165                 170                 175

Arg Val Ala Ala Gly Ala Tyr Lys Glu Leu Glu Phe Val Lys Ile Lys
            180                 185                 190

Gly Leu Ile Leu His Gln Pro Tyr Phe Ser Gly Lys Asn Arg Thr Glu
        195                 200                 205

Ser Glu Glu Lys Leu Lys Asp Gln Leu Leu Pro Leu His Ala Ile
    210                 215                 220

Asp Lys Met Phe Asp Leu Ser Leu Pro Lys Gly Thr Leu Asp His Asp
225                 230                 235                 240

His Glu Tyr Ser Asn Pro Phe Leu Asn Gly Gly Ser Lys His Leu Asp
                245                 250                 255

Asp Val Ile Ala Gln Gly Trp Lys Ile Leu Val Thr Gly Val Ser Gly
            260                 265                 270

Asp Pro Leu Val Asp Asn Ala Arg Asn Phe Ala Asn Phe Met Glu Glu
        275                 280                 285

Lys Gly Ile Lys Thr Phe Lys Leu Phe Gly Asp Gly Tyr His Ala Ile
    290                 295                 300
```

-continued

```
Glu Gly Phe Glu Pro Ser Lys Ala Ala Ala Leu Ile Gly Ala Thr Lys
305                 310                315                320

Asp Phe Ile Cys Ala Thr Thr Asn
                325
```

INCOMPATIBLE PLANT AND PATHOGEN INTERACTION RELATED GENE

BACKGROUND OF THE INVENTION

The present invention relates to a cDNA clone, designated to icc13 (incompatible *Capsicum annuun-Colletotrichum gloeosporioides* interactions) gene and individual component; thereof including its coding region and its gene product; modification thereto; application of said gene, coding region and modifications thereto; DNA construct, vectors and transformed plants each comprising the gene or part thereof.

Plants are continuously threatened by fungi and other microbial pathogens and deploy a number of strategies to defend them against pathogen infection. The defense responses are complex and include the formation of antimicrobial phytoalexins (Van Etten et al., 1989) and pathogenesis-related (PR) proteins (Linthorst, 1991; Ponstein et al., 1994), and the deposition of lignin to cell wall (Dean and Kúc, 1988). One of the most efficient ways of disease resistant reactions against potential pathogens is the hypersensitive reaction (HR). HR prevents further invasion and colonization of pathogens, which is known to be incompatible interactions between plant and pathogen (Goodman and Novacky, 1994).

Fruit ripening represents a genetically synchronized system that involves development unique to plant species. The phenomenon of ripening includes changes in color, texture, respiration rates, flavor, and aroma (Giovannoni, 1993). Generally, ripe fruit increases susceptibility to pathogen infection (Prusky et al., 1991; Swinburn, 1983). Therefore, fruits as one of the reproductive organs of plants need protection against pathogens to maintain fruit integrity and seed maturation. The expression of PR proteins is developmentally regulated during the formation of flower and fruit (Neal et al., 1990; Tattersall et al., 1997). Recently, several antifungal proteins that are responsible for protection against pathogens during fruit ripening were identified (Fils-Lycaon et al., 1996; Meyer et al., 1996; Salzman et al., 1998).

*Colletotrichuin gloeosporioides* (Penz.) is the casual agent of anthracnose diseases on fruit crops (Daykin, 1984; Dodd et al., 1991; Prusky et al., 1991) such as pepper (*Capsicum annuuin L.*) (Kim et al., 1986; Manandhar et al, 1995). In order to successfully infect the host plants, the fungus produces the appressorium from the germinating conidium. Subsequently, an infection hypha from the appressorium penetrates the cuticle and epidermal cell of the host surfaces. In Colletotrichum fungi, the topography of the plant surface was thought to be a physical signal for inducing the appressorial formation (Staples and Macko, 1980). The surface wax of avocado fruit was reported to act as a chemical signal for the appressorial formation in *C. gloeosporioides* (Podila et al., 1993). The genes expressed during the appressorium formation of *C. gloeosporioides* induced by the host surface wax were cloned (Hwang and Kollatukudy, 1995). However, plant responses to the formation of appressorium and infection hypha of the fungus has not been studied.

In our previous study, we found that an isolate of *C. gloeosporioides* showed the incompatible interactions with ripe-red pepper fruit and the compatible interactions with unripe-mature-green fruit (Oh et al., 1998). To investigate the molecular mechanism involved in the incompatible interactions between pepper and *C. gloeosporioides*, we isolated the icc13 cDNA that is specifically expressed in the ripe fruit of pepper, but not in the unripe fruit, using mRNA differential display method. The expression of icc13 gene was studied based on fungal morphogenesis in the initial infection process during the incompatible interactions. We also found that the icc13 mRNA is induced by wounding and exogenous jasmonic acid during ripening.

SUMMARY OF THE INVENTION

The object of the present invention is to provide an isolated cDNA clone encoding for ICC13 protein from *Capsicum annuuin* having nucleotide sequence as shown in SEQ ID No. 1, and an ICC13 protein from the incompatible interactions between plant and microorganism encoded by said cDNA sequence number 22 to 1005 of said cDNA clone having amino acid sequence as shown in SEQ ID No. 2.

Another object of the present invention is to provide a protein from the incompatible interactions between plant and microorganism, wherein the amino acid sequence has at least 80% homology to said ICC13 protein, and a protein from the incompatible interactions between plant and microorganism comprising pentapeptide motifs -His-Gly-Gly-Gly-Phe- and -Gly-X-Ser-X-Gly- same as said protein, wherein X means any amino acid.

The further object of the present invention is to provide a protein comprising the amino acid sequence obtained by the expression of a modified recombinant DNA sequence.

The present invention relates to a cDNA clone, designated to icc13, the sequence of which is depicted in SEQ ID No. 1. The anthracnose fungus, *Colletotrichum gloeosporioides*, was previously shown to have incompatible interactions with the ripe fruit of pepper (*Capsicum annuum*). We isolated a novel gene icc13 from this incompatible interaction using mRNA differential display method. The amino acid sequence of the encoded protein (SEQ ID No. 2) showed limited but significant sequence homology to both lipases and esterases of prokaryotic organisms, and contains the HGGGF and GXSXG motifs as well as the catalytic triads of amino acid residues. The icc13 gene was highly expressed in the ripe fruit at 48 h after infection with the fungus, but was not expressed in the unripe fruit that showed compatible interactions. The examination of the fungal morphogenesis showed that infection hypha from appressorium invaded and colonized the epidermal cells of the unripe fruit, but not on those of the ripe fruit. These results suggest that the icc13 gene product may be involved in a defense mechanism against the fungal invasion and colonization after infection hypha penetrated into the outer-epidermal cells of the fruit. In addition, the icc13 mRNA was induced only in the ripe fruit by wounding and jasmonic acid treatment. The icc13 gene can be cloned into an expression vector to produce a recombinant DNA expression system suitable for insertion into cells to form a transgenic plant transformed with this gene. The icc13 gene of this invention can be also used to produce transgenic plants which exhibit enhanced resistance against phytopathogens, including fungi, bacteria, viruses, nematodes, mycoplasmalike organisms, parasitic higher plants, flagellate protozoa, and insects.

BRIEF DESCRIPTION OF THE DRAWINGS

FIG. 1. Nucleotide and deduced amino acid sequences of the putative ICC13 cDNA. Potential polyadenylation signals at nucleotide position 1059 and 1086 are underlined.

FIG. 2. Alignment of the deduced amino acid sequence from ICC13 cDNA (Pep) (Genbank AF072533) to four other proteins containing the HGGGF and GXSXG motifs. Two unknown proteins from Arabidopsis (Ara) (Genbank AC003680), the hsr203J protein from *Nicotiana tabacum* (Tob) (Genbank X77136), and a lipase-like enzyme from a bacterium *Alcaligenes eutrophus* (Bac) (Genbank L36817). The motifs HGGGF and GXSXG are indicated by dots and the components of the catalytic triad, Ser, Asp, and His are indicated by asterisks (*).

FIG. 5. Induction of icc13 from ripe fruit by exogenous JA treatment and wounding. RNAs were isolated from unripe fruit (U) and ripe fruit (R) 1, 3, 6, and 24 h after JA treatment at 40 μM and after wounding. The icc13 gene was not induced from unripe fruit treated.

DETAILED DESCRIPTION OF THE INVENTION

The present invention has identified a cDNA clone, designated to icc13, from the incompatible pepper and the pepper anthracnose fungus *Colletotrichum gloeosporioides* interaction using mRNA differential display method and cDNA library screening. The icc13 cDNA contains 1217 bp nucleotides in length with 21 bp of 5'-untranslated region and 212 bp of 3'-untranslated region including the poly (A) tail (FIG. 1). The nucleotide sequences contained one-open reading frame from nucleotide numbers 22 to 1005 encoding a polypeptide of 36.4 kDa with 328 amino acids. The ICC13 protein contains the His-Gly-Gly-Gly-Phe- (-HGGGF-) and Gly-Ser-Ser-Cys-Gly- (-GSSCG-) motifs as well as the catalytic triads of amino acid residues. The pentapeptide -HGGGF- is found in many lipases and esterases from bacteria and manunals (Kok et al., 1993; Langin et al., 1993) and GXGSXG- found in many member of the serine hydrolase (Feller et al., 1991). The ICC13 protein also contains potential catalytic triad of lipases, Asp and His with the conserved Ser in the GXSXG. These results suggest that ICC13 protein is a member of the lipase and esterase enzyme family.

Figure 3:
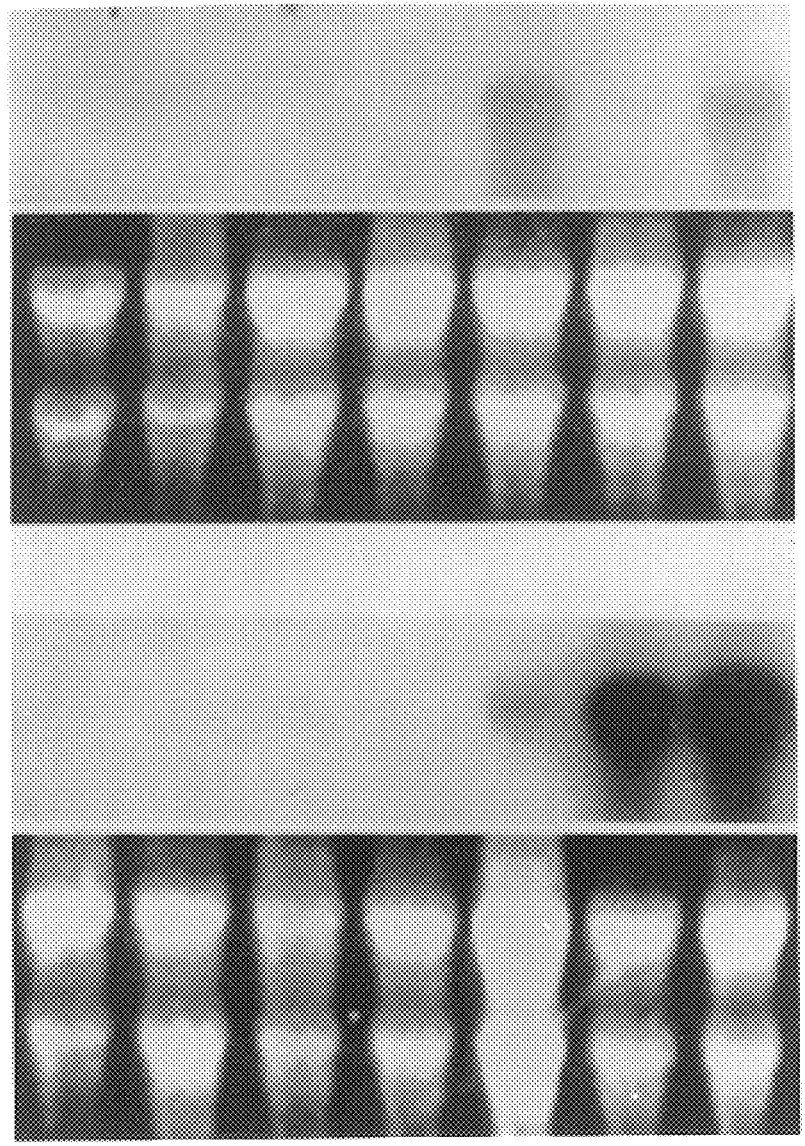
FIG. 3. Induction of icc13 by *Colletotrichum gloeosporioides* infections from unripe and ripe pepper fruits. RNA blot analysis of icc13 gene expression following the fungal infection from unripe fruit (UF/fungus—compatible interactions) and ripe fruit (RF/fungus—incompatible interactions). Time is indicated in h after inoculation. Ger.: conidial germination, App.: appressorial formation, Hyp.: infection hypha formation, Inv.: infection hypha invasion, and Sym.: initial anthracnose symptoms only on unripe fruit.

To examine the time-course of the induction of icc13 mRNA after the fungal infection, RNA blots analysis was performed with both ripe and unripe fruits at 0, 3, 6, 12, 24, 48, and 72 h using icc13 cDNA as a probe (FIG. 3). The icc13 mRNA was not detectable in uninoculated unripe and ripe fruits. The icc13 mRNA was detected at low level in both fruits after 24 h and highly induced only in the ripe fruit after 48 h. In the unripe fruit, icc13 mRNA remain at low level even after 48 h. These results showed that the icc13 gene is highly expressed only in incompatible pepper/anthracnose fungus interactions.

Figure 4:
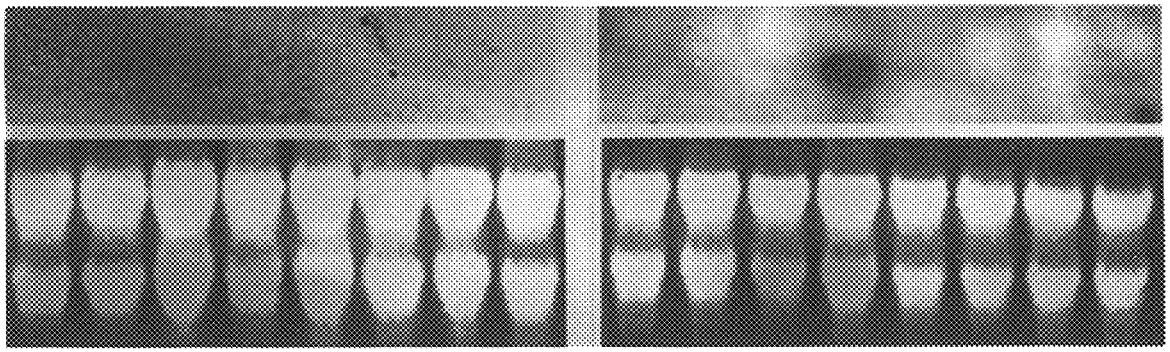
FIG. 4. Induction of icc13 from ripe fruit by exogenous JA treatment. RNAs were isolated from both unripe (U) and ripe (R) fruits treated with SA (1=0.5 mM, 2=5 mM), ABA (3=4 μM, 4=40 μM), JA (5=4 μM, 6=40 μM) and ethylene (7=1 mM, 8=10 mM) for 24 h.

To identify the inducers of icc13 gene expression, RNA gel blot analysis was performed with both ripe and unripe fruits treated with exogenous abscisic acid (ABA), ethylene, jasmonic acid (JA), and salicylic acid (SA) for 24 h. The icc13 mRNA was detected only in the ripe fruit treated with JA at 40 μM (FIG. 4). Higher concentrations of JA at 100, 400, and 1000 μM was not able to induce the expression of icc13 from unripe fruit (data not shown). Moreover, neither of ABA, ethylene, and SA did affect the expression of the icc13 gene in both ripe and unripe fruits.

Figure 6:
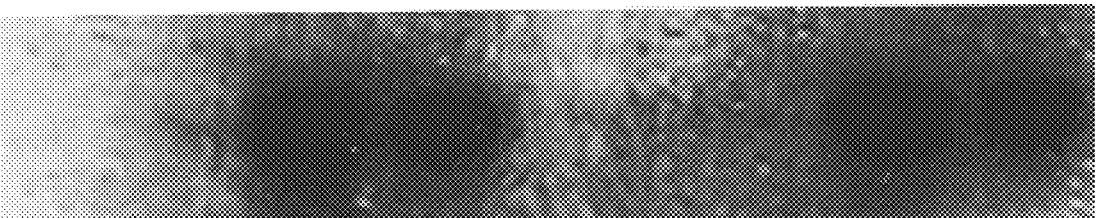
FIG. 6. Fruit-specific induction of icc13 by *Colletotrichum gloeosporioides* infections and wounding. RNAs were isolated from unripe fruit (U), ripe fruit (R), leaf, root, and stem at 24 h after fungal inoculation, and at 24 h and 48 h after wounding. The icc13 gene was not induced from leaf, stem, and root by fungal inoculation and wounding.

To test whether the icc13 is induced in fruit by JA and wounding before 24 h, the fruits were treated with JA and by wounding for 1, 3, 6, and 24 h. The induction of icc13 by JA was detected only from the ripe fruit after 24 h treatment, but not from the unripe fruit (data not shown) (FIG. 5). In addition, the induction of icc13 by wounding was observed at low levels after 6 h treatment and at high levels after 24 h only from the ripe fruit, but not from the unripe fruit (data not shown). RNA blot analysis was also performed with various organs inoculated with the fungus and treated by wounding. The icc13 mRNA was induced in both ripe and unripe fruits infected by the fungus but only in the ripe fruit by wounding (FIG. 6). In leaves, stems, and roots, the icc13 mRNA was not induced by fungal inoculation and wounding (data not shown). Our study showed that the expression of icc13 by JA and wounding is upregulated during ripening. We suggest that the icc13 gene is involved in the defense mechanism in the ripening fruit against pathogens or wound for fruit integrity and seed maturation.

These studies suggest that the pepper esterase ICC13 may play an important role during the incompatible plant-pathogen interactions to confer disease resistance to the plant.

The icc13 gene can be cloned into an expression vector to produce a recombinant DNA expression system suitable for insertion into cells to form a transgenic plant transformed with this gene. The icc13 gene of this invention can be also used to produce transgenic plants which exhibit enhanced resistance against phytopathogens, including fungi, bacteria, viruses, nematodes, mycoplasmalike organisms, parasitic higher plants, flagellate protozoa, and insects.

EXAMPLES

Plant Material and the Fungus

Ripe-red fruits and unripe-mature-green of pepper cv Nokkwang were grown and harvested under green-house conditions. Ten μl at 5×10$^5$/ml of monoconidial isolate KG13 of *C. gloeosporioides* was used for the inoculation of both fruits as described (Oh et al., 1998). The numbers of conidium, appressorium, and infection hypha on the fruit surface were counted at 3, 6, and 12 h after inoculation, respectively, and the length of infection hypha was measured at 24 h after inoculation. More than 100 conidia per sample were observed and the microscopic observation was done three times with five replicates each.

Plant Treatments

For wound treatment, five healthy ripe and unripe fruits were deeply scratched by a knife and incubated for 24 and 48 h under relative humidity of 100% at 27° C. in the dark. Ten μl of salicylic acid (SA) at 0.5 and 5 mM, abscisic acid (ABA) at 4 and 40 μM, and jasmonic acid (JA) 4 and 40 μM, and ethylene at 1 and 10 mM were applied to both ripe and unripe sets of five fruits, respectively. After 24 h incubation under the condition described above, the fruits were excised to 1 cm² at the application site and frozen in liquid nitrogen. Leaf, root, and stem samples were harvested from 3-week-old plants and handled as described above for wounding and fungal inoculation.

mRNA Differential Display

Total RNA was extracted from healthy and infected ripe and unripe fruits using RNeasy Plant kit (Qiagen, Germany) according to the manufacturer's instruction. We used total RNA as template for the reverse transcriptase reaction and performed differential display with [$\alpha^{33}$P]dATP instead of [$\alpha^{35}$S]dATP (Liang and Pardee, 1992). Anchored primers and random-arbitrary primers were purchased from Operon Technologies (Alameda, Calif., USA). PCR-amplified cDNA fragments were separated on denaturing 5% polyacrylamide gels in Tris-borate buffer. cDNAs were recovered from the gel, amplified by PCR, and cloned into pGEM-T easy vector (Promega, USA) as described (Oh et al., 1995).

Construction and Screening of cDNA Library

Poly(A)⁺ mRNA was purified from total RNA of unripe-green fruits at 24 and 48 h after inoculation with *C. gloeosporioides* using Oligotex mRNA Kit (Qiagen, Germany). The cDNA library (2.5×10⁵ plaque-forming unit with the mean insert size of 1.2 kb) was constructed in the cloning vector λZAPII (Stratagene, Germany) according to the manufacturer's instruction.

A partial cDNA, designated ddPC13, from the differential display was used as a probe to screen the *C. gloeosporioides*-induced pepper cDNA library. After three rounds of plaque hybridization, positive plaques were purified. The pBluescript SK phagemid containing cDNAs was excised in vivo from the ZAP Express vector using the ExAssit helper phage.

DNA Sequencing and Homology Search

The cDNA sequencing was performed with an ALFexpress automated DNA sequencer (Pharmacia, Sweden). Analysis of nucleotide and amino acid sequences and a multiple sequence analysis were performed using the DNA-SIS sequence analysis software for Windows, version 2.1 (Hitachi, Japan). For a homology search, cDNA sequence was compared to the NCBI non-redundant databases using the BLAST electronic mail server (Altschul et al., 1997)

RNA Blot and Hybridization

Total RNA (10 μg/lane) from each plant tissue used in this study was separated on 1.2% denaturing agarose gels in the presence of formaldehyde. RNA gel-blotting, hybridization and washing were conducted as described by the manufacturer of the positively charged nylon membrane employed (Hybond N⁺; Amersham, UK). Radiolabeled probes were prepared with [$\alpha$-$^{32}$P]dCTP (Amersham) using a random primer-labeling kit (Boehringer Mannheim, Germany).

Isolation and Characterization of icc13 cDNA

To isolate the mRNAs induced in the pepper from the incompatible interactions with anthracnose fungus, total RNA was prepared from both compatible interactions of unripe-mature-green fruits and incompatible interaction of ripe-red fruits with the fungal inoculation (Oh et al., 1998). Total RNA was then used for mRNA differential display, and several cDNA fragments amplified from the ripe fruit but not from the unripe fruit with the fungal inoculation were cloned. The RNA gel blot analysis showed that a transcript of 1.2 kb, hybridized by one of the cDNA fragments amplified, was highly accumulated by the incompatible interactions. To isolate the full-length cDNA clone, this cDNA fragment was used as a probe for plaque hybridization using a cDNA library prepared from unripe fruits at 24 and 48 h after inoculation with the fungus. A clone which gave a strong signal from plaque hybridization was designated pICC13 (incompatible *Capsicum annuum/Colletotricum gloeosporioides* interactions), isolated and sequenced (FIG. 1).

The pICC13 cDNA contains 1217 bp nucleotides in length with 21 bp of 5'-untranslated region and 212 bp of 3'-untranslated region including the poly (A) tail (Genbank AF072533). The pICC13 clone represents a near full-length cDNA of the 1.2 kb gene transcript recognized by RNA gel blot analysis. The nucleotide sequences contained one open reading frame from nucleotide numbers 22 to 1005 encoding a polypeptide of 36.4 kDa with 328 amino acids. The 3'-untranslated region contained two putative polyadenylation sites approximately at 116 and 90 nucleotides upstream from the poly (A) tail.

Alignment of the amino acid sequences of ICC13 protein and four other proteins is shown in FIG. 2. The ICC13 protein was found to have significant amino acid sequence homology to the hsr203J protein, a tobacco esterase induced from the incompatible interaction with a phytopathogenic bacterium (sequence identity and similarity: 32% and 48%, respectively) from *Nicotiana tabacum* (Pontier et al., 1994), and a lipaselike enzyme (26% and 38%) from the aerobic bacterium *Alcaligenes eutrophus* (Valentin et al., 1995). The ICC13 protein also has high sequence homology to two unknown proteins (37% and 54%, for F17K2.14; 35% and 52% for F17K2.13) from Arabidopsis (GenBank AC003680). The ICC13 protein contains the pentapeptide -His-Gly-Gly-Gly-Phe- (-HGGGF-) (amino acids 86–90) that are found in many lipases and esterases from bacteria and mammals (Kok et al., 1993; Langin et al., 1993) and -Gly-Ser-Ser-Cys-Gly- (-GSSCG-) (amino acids 163–167), the consensus motif GXSXG found in many members of the serine hydrolase (Feller et al., 1991). The ICC13 protein also contains potential catalytic triad of lipases, Asp and His with the conserved Ser in the GXSXG. These results suggest that ICC13 protein is a member of the lipase and esterase enzyme family.

The fungus-inducible icc13 gene product shows amino acid sequence homology to hsr203J gene product, the tobacco esterase which is induced from the incompatible interactions between tobacco and a pathogenic bacterium, *Pseudomonas solanacearum* (Baudouin et al., 1997; Pontier et al., 1994). The consensus HGGGF and GXSXG motifs and the catalytic triad in lipases and esterases are also found in the ICC13 protein. The Ser in the GXSXG, and Asp and His at the C-terminus of hormone-sensitive lipases have been demonstrated to be essential for the catalytic activities of the enzyme (Contreras et al., 1996; Osterlund et al., 1997). The HGGGF and GXSXG motifs were found in the expressed sequence tags from plant (Baudouin et al., 1997), although the physiological role of the enzyme is not clear. A putative role of HSR203J has been suggested to be involved in detoxification process preventing damage by oxidative stress during HR. These studies suggest that the pepper esterase ICC13 may play an important role during the incompatible plant-pathogen interactions to confer disease resistance to the plant.

Induction of icc13 by Fungal Infection

*C. gloeosporioides* infects pepper fruit through conidial germination, appressorial formation and infection hypha formation on fruit surfaces. In order to observe the differential fungal behaviors on the surfaces of ripe and unripe fruits, the time-course of fungal morphogenesis was examined after the pepper fruits were inoculated with the fungus. The conidia of the fungus started to germinate within 2 h after inoculation (data not shown) and over 58% of conidia were germinated on both ripe and unripe fruits after 3 h (Table I). After 6 h, over 56% of conidia produced immature appressoria from germinating conidia. While the formation of infection hypha from mature appressoria containing melanin pigments was observed on both fruits after 12 h, the formation of appressoria and infection hypha was higher in the compatible interactions than in the incompatible interactions during the early fungal infection process. After 24 h, longer infection hypha from appressoria invaded and colonized the epidermal cells of the unripe fruit, but did not affect those of the ripe fruit. Initial anthracnose symptoms were detected only on the unripe fruit after 48 h, and a typical sunken necrosis occurred within 120 h (Oh et al., 1998).

Table I.

Mean percent of conidial germination, appressorial formation, and infection hypha formation, and mean length of infection hypha of *Colletotrichum gloeosporioides* on unripe-mature-green and ripe-red fruits of pepper (*Capsicum annuum*)

| | Hours after inoculation | | | |
|---|---|---|---|---|
| | 3 | 6 | 12 | 24 |
| | Conidial germination (%) | Appressorial formation (%) | Infection hypha formation (%) | Length of infection hypha (%) |
| Fruit | | | | |
| Unripe-mature-green fruit | 64.4 (±11) | 80.3 (±97) | 26.2 (±10.2) | 8.5 (±1.9) |
| Ripe-red fruit | 58.8 (±10.3) | 56.5 (±17) | 4.5 (±2.5) | 7.2 (±1.9) |

Percents of conidial germination, appressorial formation, and infection hypha formation were determined as the number of germinated conidia, appressoria, and infection hypha divided by the total number of conidia observed and multiplied by 100. The length of infection hypha from appressoria to penetration of cuticular layers of fruits was measured under a microscope. The observation was repeated three times with five replicates each. More than 100 conidia per sample were observed. Numbers indicate the mean value of three observations and ± indicates standard deviations.

The infection of *C. gloeosporioides* is achieved through conidial germination, appressorial formation, and infection hyphae formation which are necessary for subsequent cuticular penetration (Bailey et al., 1992). A microscopic analysis showed that germinating conidia did not reveal any significant differences on both ripe and unripe pepper fruits 3 h after infection. However, high levels of the formation of appressorium and infection hypha, and longer infection hypha were observed on the unripe fruit than on the ripe fruit after 6 h of infection. In other studies, the germination and appressorial formation were higher on the unripe-resistant pepper fruit than on the ripe-susceptible fruit inoculated with *C. capsici* or *Glomerella cingulata* (Adikaram et al., 1983). The germination of spores was similar on both ripe and unripe fruits, although the unripe banana fruit stimulated appressorial formation of *C. musae* (Swinburne, 1976). In avocado and *C. gloeosporioides* interactions, conidial germination and appressorial formation were similar on unripe-resistant and ripe-susceptible fruits (Prusky and Saka, 1989; Prusky et al., 1991). These studies suggest that conidial germination and appressorial formation are not important factors to determine resistant/susceptible interactions between pre- and post-ripening stages of the host fruit and the Colletotrichum fungus, although conidial germination and appressorial formation are prerequisite to infect host plant.

To examine the time-course of the induction of icc13 mRNA after the fungal infection, RNA blots analysis was performed with both ripe and unripe fruits at 0, 3, 6, 12, 24, 48, and 72 h using icc13 cDNA as a probe (FIG. 3). The icc13 mRNA was not detectable in uninoculated unripe and ripe fruits. The icc13 mRNA was detected at low level in both fruits after 24 h and highly induced only in the ripe fruit after 48 h. In the unripe fruit, icc13 mRNA remain at low level even after 48 h. These results showed that the icc13 gene is highly expressed only in incompatible pepper/anthracnose fungus interactions.

Our study in plant response to infection hypha of the fungus showed that the icc13 mRNA was induced after 24 h of infection when the infection hypha penetrated the cuticle layer of the ripe and unripe pepper fruits. This gene was highly expressed only from the ripe fruit, but not from the unripe fruit after 48 h of infection when the infection hypha colonized the epidermal cells of the unripe fruit. Since the icc13 gene is expressed after 24 h of infection, ICC13 may be involved in defense response against the infection hypha penetrating into the outer-epidermal cells of pepper fruit. Taken together, we suggest that in the early infection process by *C. gloeosporioides*, the interactions between the fruit ripening and the infection hypha determine the compatibility or incompatibility of the plant-pathogen interactions.

Induction of icc13 in Ripe Fruit by Jasmonic Acid and Wounding

To identify the inducers of icc13 gene expression, RNA gel blot analysis was performed with both ripe and unripe fruits treated with exogenous ABA, ethylene, JA, and SA for 24 h. The icc13 mRNA was detected only in the ripe fruit treated with JA at 40$\mu$M (FIG. 4). Higher concentrations of JA at 100, 400, and 1000 $\mu$M was not able to induce the expression of icc13 from unripe fruit (data not shown). Moreover, neither of ABA, ethylene, and SA did affect the expression of the icc13 gene in both ripe and unripe fruits.

To test whether the icc13 is induced in fruit by JA and wounding before 24 h, the fruits were treated with JA and by wounding for 1, 3, 6, and 24 h. The induction of icc13 by JA was detected only from the ripe fruit after 24 h treatment, but not from the unripe fruit (data not shown) (FIG. 5). In addition, the induction of icc13 by wounding was observed at low levels after 6 h treatment and at high levels after 24 h only from the ripe fruit, but not from the unripe fruit (data not shown).

RNA blot analysis was also performed with various organs inoculated with the fungus and treated by wounding. The icc13 mRNA was induced in both ripe and unripe fruits infected by the fungus but only in the ripe fruit by wounding (FIG. 6). In leaves, stems, and roots, the icc13 mRNA was not induced by fungal inoculation and wounding (data not shown).

The fungus-induced expression of icc13 gene during the incompatible interactions was also observed by JA treatment and wounding of the ripe fruit (FIGS. 4 and 6). JA is a plant hormone functionally responsible for mechanical wounding responses (Creelman et al., 1992, Creelman and Mullet, 1997). It also activates genes for plant disease resistance Johnson et al., 1989; Xu et al., 1994; Reinbothe et al., 1994). Although methyl jasmonate is known to trigger the ripening process of climacteric fruits, tomato and apple fruits, with ethylene production (Czapski and Saniewski, 1992; Saniewski et al., 1987a, 1987b), the role of JA in fruit ripening is not known in nonclimacteric fruit, such as pepper, grape, pineapple, and strawberry. Our study showed that the expression of icc13 by JA and wounding is upregulated during ripening. We suggest that the icc13 gene is involved in the defense mechanism in the ripening fruit against pathogens or wound for fruit integrity and seed maturation.

REFERENCES

Adikaram N K B, Brown A E, Swinburne T R (1983) Observations on infection of *Capsicum annuum* fruit by *Gloinerella cingulata* and *Colletotrichum capsici*. Trans Brit Mycol Soc 80: 395–401

Altschul S F, Madden T L, Schffer A A, Zhang J, Zhang Z, Miller W, Lipman D J (1997) Gapped BLAST and PSI-BLAST: a new generation of protein database search programs. Nucleic Acids Res 25: 3389–3402

Bailey J A, O'Connell R J, Pring R J, Nash C (1992) Infection strategies of Colletotrichum species. In JA Bailey and JA Jeger, eds, Colletotrichum: Biology, Pathology and Control. CAB International, Wallingford, UK, pp 88–120

Baudouin E, Charpenteau M, Roby D, Marco Y, Ranjeva R, Ranty B (1997) Functional expression of a tobacco gene related to the serine hydrolase family. Esterase activity towards short-chain dinitrophenyl acylesters. Eur J Biochem 248: 700–706

Contreras J A, Karlsson M, Osterlund T, Laurell H, Svensson A, Holm C (1996) Hormone-sensitive lipase is structurally related to acetylcholinesterase, bile salt-stimulated lipase, and several fungal lipases. J Biol Chem 271: 31426–31430

Creelman R A, Mullet J E (1997) Biosynthesis and action of jasmonates in plants. Annu Rev Plant Physiol Plant Mol Biol 48: 355–381

Creelman R A, Tierney M L, Mullet J E (1992) Jasmonic acid/methyl jasmonate accumulate in wounded soybean hypocotyls and modulate wound gene expression. Proc Natl Acad Sci USA 89: 4938–4941

Czapski J, Saniewski M (1992) Stimulation of ethylene production and ethylene-forming enzyme in fruits of the non-ripening nor and rin tomato mutants by methyl jasmonate. J Plant Physiol 139: 265–268

Daykin ME (1984) Infection in blueberry fruit by *Colletotrichum gloeosporioides*. Plant Dis 68: 984–950

Dean R A, Kc J (1988) Rapid lignification in response to wounding and infection as a mechanism for induced systemic protection in cucumber. Physiol Plant Pathol 31: 69–81

Dodd J C, Estrada A, Matcham A, Jeffries P, Jeger M J (1991) The effect of environmental factors on *Colletotrichum gloeosporioides*, the causal agent of mango anthracnose, in the Philippines. Plant Pathol 40: 568–575

Feller G, Thirty M, Gerday C (1991) Nucleotide sequence of the lipase gene lip2 from the antarctic psychrotroph Moraxella TA144 and site-specific mutagenesis of the conserved serine and histidine residues. DNA Cell Biol 10: 381–388

Fils-Lycaon B R, Wiersma P A, Eastwell K C, Sautiere P (1996) A cherry protein and its gene, abundantly expressed in ripening fruit, have been identified as thaumatin-like. Plant Physiol 111: 269–273

Giovannoni J J (1993) Molecular biology of fruit developmental and ripening. In J Bryant, ed, Methods in Plant Molecular Biology. Academic Press, N.Y., pp 253–287

Goodman R N, Novacky A J (1994) The Hypersensitive Reaction in Plants to Pathogens. A Resistance Phenomenon. APS Press, St. Paul, Minn., USA.

Hwang C-S, Kolattukudy PE (1995) Isolation and characterization of genes expressed uniquely during appressorium formation by *Colletotrichum gloeosporioides* conidia induced by the host surface wax. Mol Gen Genet 247: 282–294

Johnson R, Narvez J, An G, Ryan C (1989) Expression of proteinase inhibitors I and II in transgenic tobacco plants: Effects on natural defense against *Manduca sexta* larvae. Proc Natl Acad Sci USA 86: 9871–9875

Kim W G, Cho E K, Lee E J (1986) Two strains of *Colletotrichum gloeosporioides* Penz. causing anthracnose on pepper fruits. Korean J Plant Pathol 2: 107–113

Kok R G, Christoffels V M, Volsman B, Hellingwerf K J (1993) Growth-phase-dependent expression of the lipolytic system of *Acinetobacter calcoaceticus* BD413: cloning of a gene coding one of the esterases. J Gen Microbiol 139: 2329–2342

Langin D, Laurell H, Stenson-Holst L, Belfrage P, Holm C (1993) Gene organization and primary structure of human hormone-sensitive lipase: possible significance of a sequence homology with a lipase of Moraxella TA144, an antarctic bacterium. Proc Natl Acad Aci USA 90: 4897–4901

Liang P, Pardee AB (1992) Differential display of eukaryotic messenger RNA by means of the polymerase chain reaction. Science 257: 967–971

Linthorst H J M (1991) Pathogenesis-related proteins of plants. Crit Rev Plant Sci 10: 123–150

Manandhar J B, Hartman G L, Wang T C (1995) Conidial germination and appressorial formation of *Colletotrichum capsici* and *C. gloeosporioides* isolates from pepper. Plant Dis 79: 361–366

Meyer B, Houln G, Pozueta-Romero J, Schantz M-L, Schantz R (1996) Fruit-specific expression of a defensin-type gene family in bell pepper. Upregulation during ripening and upon wounding. Plant Physiol 112: 615–622

Neal A D, Wahleithner J A, Lund M, Bonnett H T (1990) Chitinase, beta-1,3-glucansase, osmotin, and extensin are expressed in tobacco explants during flower formation. Plant Cell 2: 673–684

Oh B J, Balint D E, Giovannoni J J (1995) A modified procedure for PCR-based differential display and demonstration of use in plants for isolation of gene related to fruit ripening. Plant Mol Biol Rep 13: 70–81

Oh B J, Kim K D, Kim Y S (1998) A microscopic characterization of the infection of green and red pepper fruits by an isolate of *Colletotrichum gloeosporioides*. J Phytopathol 146: 301–303

Osterlund T, Contreras J A, Holms C (1997) Identification of essential aspartic acid and histidine residues of hormone-sensitive lipase: apparent residues of the catalytic triad. FEBS Lett 403: 259–262

Podila G K, Rogers L M, Kolattukudy P E (1993) Chemical signals from avocado surface wax trigger germination and appressorium formation in *Colletotrichum gloeosporioides*. Plant Physiol 103: 267–272

Ponstein A S, Bres-Vloemans S A, Sela-Buurlage M B, van den Elzen P J M, Melchers L S, Cornelissen B J C (1994) A novel pathogen- and wound-inducible tobacco (*Nicotiana tabacum*) protein with antifungal activity. Plant Physiol 104: 109–118

Pontier D, Godlard L, Marco Y, Roby D (1994) hsr203J, a tobacco gene whose activation is rapid, highly localized and specific for incompatible plant/pathogen interactions. Plant J 5: 507–521

Prusky D, Plumbley R A, Kobiler I (1991) The relationship between the antifungal diene levels and fungal inhibition during quiescent infections of *Colletotrichum gloeosporioides* in unripe avocado fruits. Plant Pathol 40: 45–52

Prusky D, Saka H (1989) The role of epicuticular wax of avocado fruit in appressoria formation of *Colletotrichum gloeosporioides*. Phytoparastica 17: 140

Reinbothe S, Reinbothe C, Lehman J, Becker W, Apel K, Parthier B (1994) JIP60, a methyl jasmonate-induced ribosome-inactivating protein involved in plant stress reactions. Proc Natl Acad Aci USA 91: 7012–7016

Salzman R A, Tikhonova I, Bordelon B P, Hasegawa P M, Bressan R A (1998) Coordinate accumulation of antifungal proteins and hexoses constitutes a developmentally controlled defense response during fruit ripening in grape. Plant Physiol 117: 465–472

Saniewski M, Czapski J, Nowacki J, Lange E (1987) The effect of methyl jasmonate on ethylene and 1-aminocyclopropane-1-carboxylic acid production in apple fruits. Biol Plant 29: 199–203

Saniewski M, Nowacki J, Czapski J (1987) The effect of methyl jasmonate on ethylene production and ethylene-forming enzyme activity in tomatoes. J Plant Physiol 129: 175–180

Staples R C, Macko V (1980) Formation of infection structures as a recognition response in fungi. Exp Mycol 4: 2–16

Swinburne T R (1976) Stimulants of germination and appressoria formation by *Colletotridzuin musae* (Berk. & Curt.) Arx. in banana leachate. Phytopathol Z 87: 74–90

Swinburne T R (1983) Post-Harvest Pathology of Fruits and Vegetables. Academic Press, N.Y., USA.

Tattersall D. B., van Heeswijck R, Bordier Hoj P (1997) Identification and characterization of a fruit-specific, thaumatin-like protein that accumulates at very high levels in conjunction with the onset of sugar accumulation and berry softening in grapes. Plant Physiol 114: 759–769

Valentin H E, Zwingmann G, Schonebaum A, Steinbuchel A (1995) Metabolic pathway for biosynthesis of poly (3-hydroxybutyrate-co-4-hydroxybutyrate) from 4-hydroxybutrate by *Alcaligenes eutrophus*. Eur J Biochem 227: 43–60

Van Etten H D, Matthews D E, Matthews P S (1989) Phytoalexin detoxification: Importance for pathogenicity and practical implications. Annu Rev Phytopathol 27: 143–164

Xu Y, Chang PFL, Liu D, Narasimhan ML, Raghothama K G, Hasegawa P M, Bressan, R A (1994) Plant defense genes are synergistically induced by ethylene and methyl jasmonate. Plant Cell 6: 1077–1085

What is claimed is:

1. An isolated cDNA clone encoding for incompatible *Capsicum annuum-Colletotrichum gloeosporiodes* interactions (ICC13) protein from *Capsicum annuum* having a nucleotide sequence as shown in SEQ ID No. 1.

* * * * *